United States Patent [19]

Dennehey et al.

[11] Patent Number: 4,936,820

[45] Date of Patent: Jun. 26, 1990

[54] HIGH VOLUME CENTRIFUGAL FLUID PROCESSING SYSTEM AND METHOD FOR CULTURED CELL SUSPENSIONS AND THE LIKE

[75] Inventors: T. Michael Dennehey, Arlington Heights; Stanley J. Pernic, Round Lake; Joseph C. West, Jr., Vernon Hills, all of Ill.

[73] Assignee: Baxter International Inc., Deerfield, Ill.

[21] Appl. No.: 404,008

[22] Filed: Sep. 5, 1989

Related U.S. Application Data

[63] Continuation of Ser. No. 255,126, Oct. 7, 1988, abandoned.

[51] Int. Cl.$^5$ .............................................. B04B 11/02
[52] U.S. Cl. .......................................... 494/1; 494/10; 494/18; 494/37; 494/42; 494/45
[58] Field of Search ...................... 494/1, 5, 10, 18, 21, 494/22, 37, 45, 42, 50, 35, 85; 604/6; 422/72

[56] References Cited

U.S. PATENT DOCUMENTS

| | | |
|---|---|---|
| 1,954,676 | 8/1931 | Lindberg . |
| 2,261,394 | 5/1938 | Lindgren . |
| 2,269,716 | 11/1939 | Gregg . |
| 2,321,144 | 2/1940 | Jones . |
| 2,662,687 | 4/1950 | Spross . |
| 2,719,668 | 8/1953 | Bergner . |
| 3,096,282 | 12/1957 | Trotter, Jr. . |
| 3,698,626 | 10/1972 | Kotrappa et al. . |
| 3,957,197 | 5/1976 | Sartory et al. . |
| 4,007,871 | 2/1977 | Jones et al. . |
| 4,010,894 | 3/1977 | Kellogg et al. . |
| 4,069,968 | 1/1978 | Herman . |
| 4,091,989 | 5/1978 | Schlutz . |
| 4,094,461 | 6/1978 | Kellogg et al. . |
| 4,113,173 | 9/1978 | Lolachi ................................ 494/18 |
| 4,120,448 | 10/1978 | Cullis . |
| 4,146,172 | 3/1979 | Cullis et al. . |
| 4,185,629 | 1/1980 | Cullis .................................... 494/1 |
| 4,187,979 | 2/1980 | Cullis .................................... 494/1 |
| 4,230,263 | 10/1980 | Westberg . |
| 4,261,507 | 4/1981 | Baumler . |
| 4,278,202 | 7/1981 | Westberg . |
| 4,303,193 | 12/1981 | Latham, Jr. . |
| 4,322,298 | 3/1982 | Persidsky . |
| 4,344,560 | 8/1982 | Iriguchi et al. . |
| 4,386,730 | 6/1983 | Mulzet . |
| 4,387,848 | 6/1983 | Kellogg et al. . |
| 4,419,089 | 12/1983 | Kolobow et al. . |
| 4,421,503 | 12/1983 | Latham, Jr. et al. . |
| 4,425,112 | 1/1984 | Ito . |
| 4,430,072 | 2/1984 | Kellogg et al. . |
| 4,439,178 | 3/1984 | Mulzet . |
| 4,445,883 | 5/1984 | Schroendorfer ..................... 494/21 |
| 4,447,221 | 5/1984 | Mulzet . |
| 4,493,691 | 1/1985 | Calari . |
| 4,531,932 | 7/1985 | Luppi et al. . |
| 4,617,009 | 10/1986 | Ohlin et al. . |
| 4,647,279 | 3/1987 | Mulzet et al. . |
| 4,668,214 | 5/1987 | Reeder ................................. 494/37 |
| 4,708,712 | 11/1987 | Mulzet . |
| 4,710,161 | 12/1987 | Takabayashi et al. . |
| 4,743,227 | 5/1988 | Takeuchi . |
| 4,772,388 | 9/1988 | Allington . |
| 4,778,444 | 10/1988 | Westberg et al. . |
| 4,790,807 | 12/1988 | Neumann et al. . |
| 4,795,314 | 1/1989 | Prybella et al. . |
| 4,798,579 | 1/1989 | Penhasi . |
| 4,806,252 | 2/1989 | Brown et al. . |
| 4,834,890 | 5/1989 | Brown et al. . |

FOREIGN PATENT DOCUMENTS

WO88/05691  8/1988  PCT Int'l Appl. .
2002266  2/1979  United Kingdom .

Primary Examiner—Robert W. Jenkins
Attorney, Agent, or Firm—Bradford R. L. Price; Paul C. Flattery; Daniel D. Ryan

[57] ABSTRACT

A centrifugal processing system for cultured cellular suspensions comprises a reservoir for pooling a desired volume of the cellular suspension from a plurality of individual containers in which the cellular suspension have been cultured. A centrifugation chamber is provided operative in response to centrifugal force for separating the cellular suspension into a cellular component and a supernatant. Fluid is conveyed from the reservoir into the centrifugation chamber at a high flow rate exceeding 1 liter per minute. The cellular component and supernatant are collected from the centrifugation chamber.

16 Claims, 6 Drawing Sheets

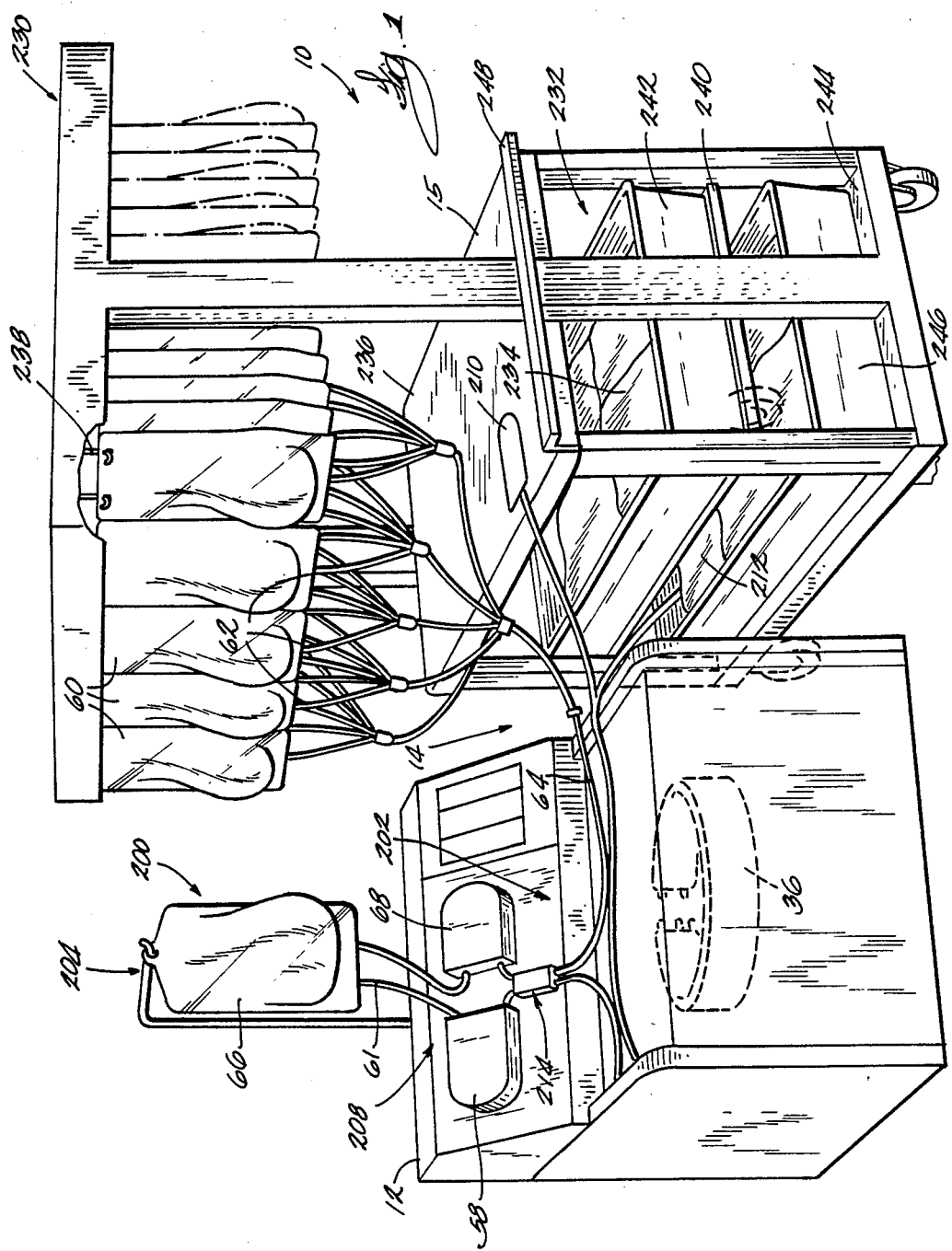

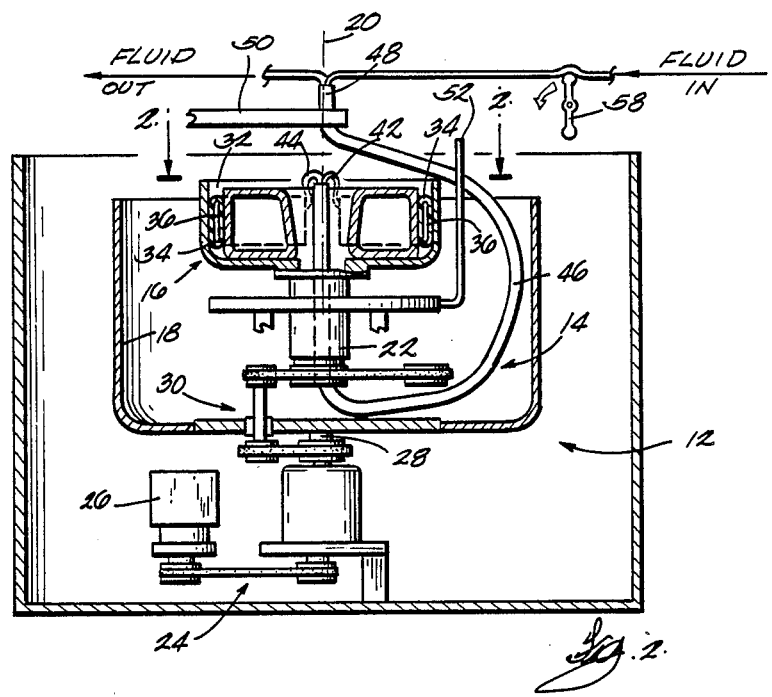
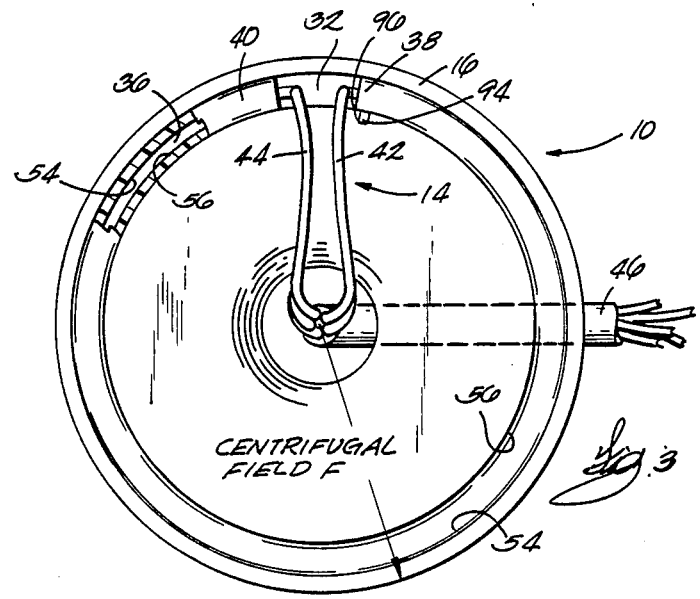

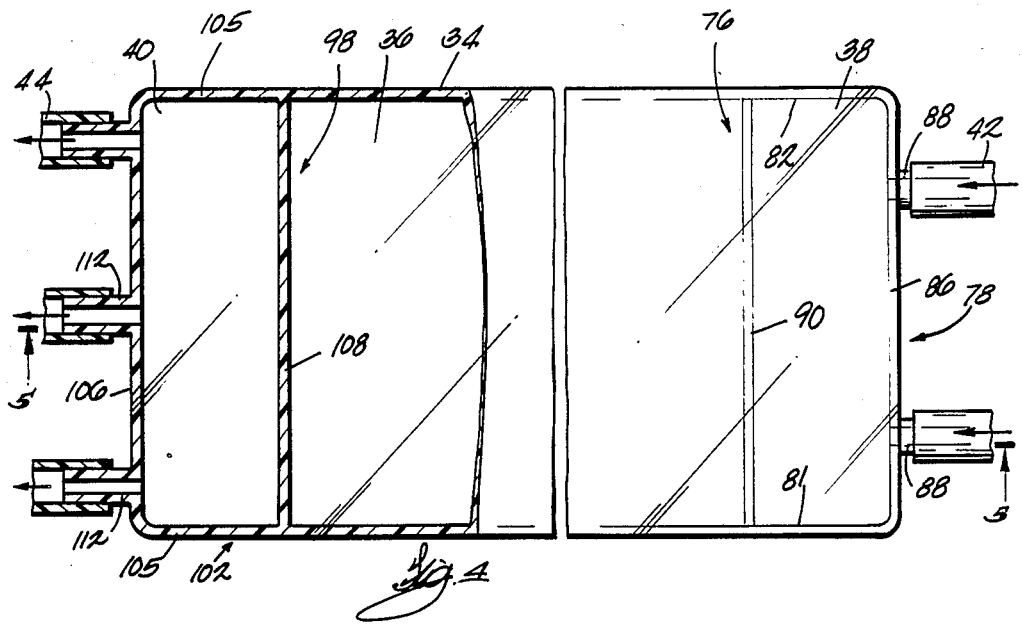
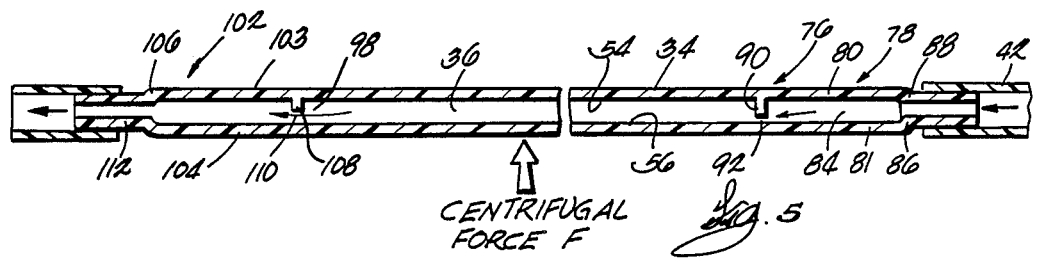
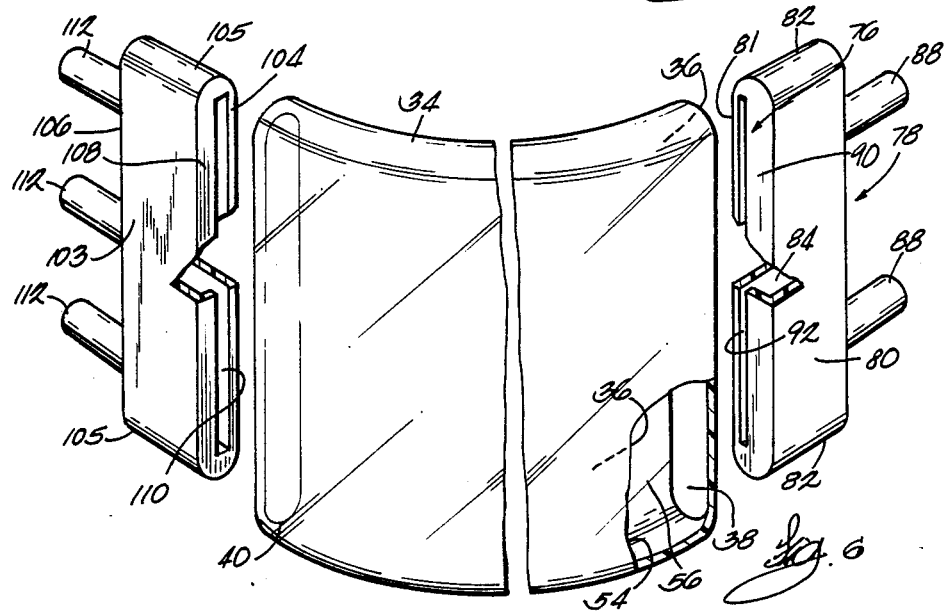

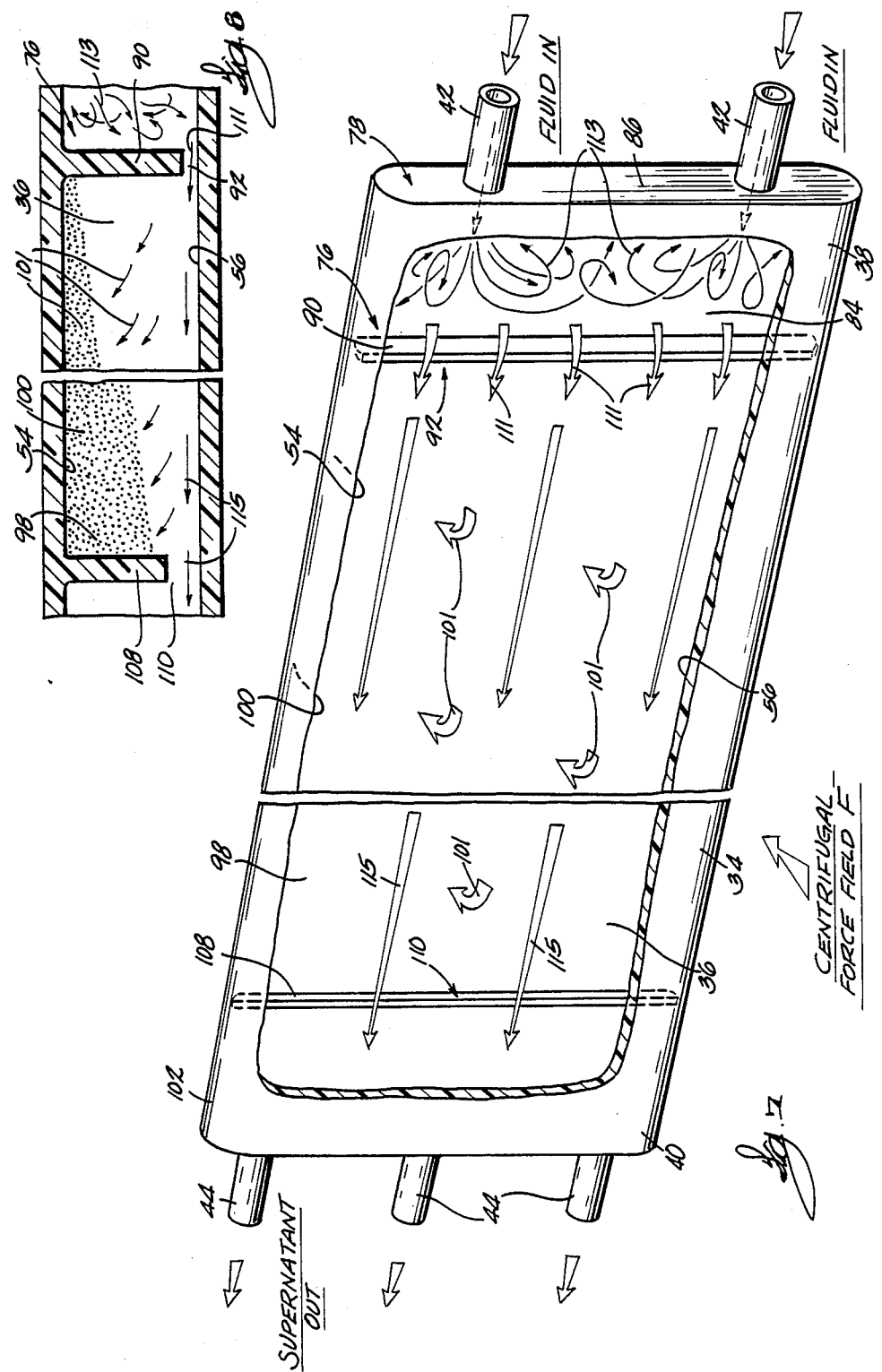

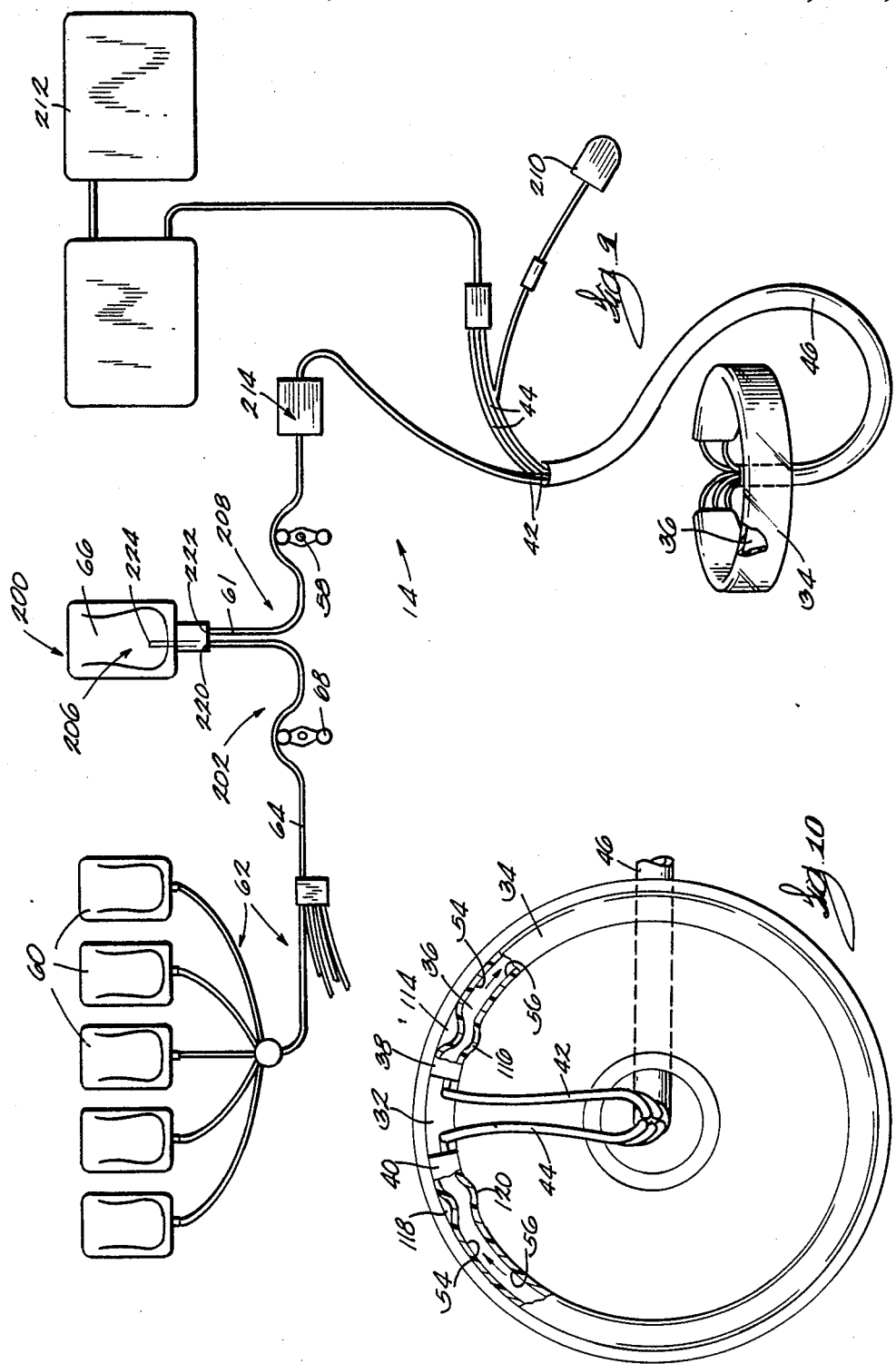

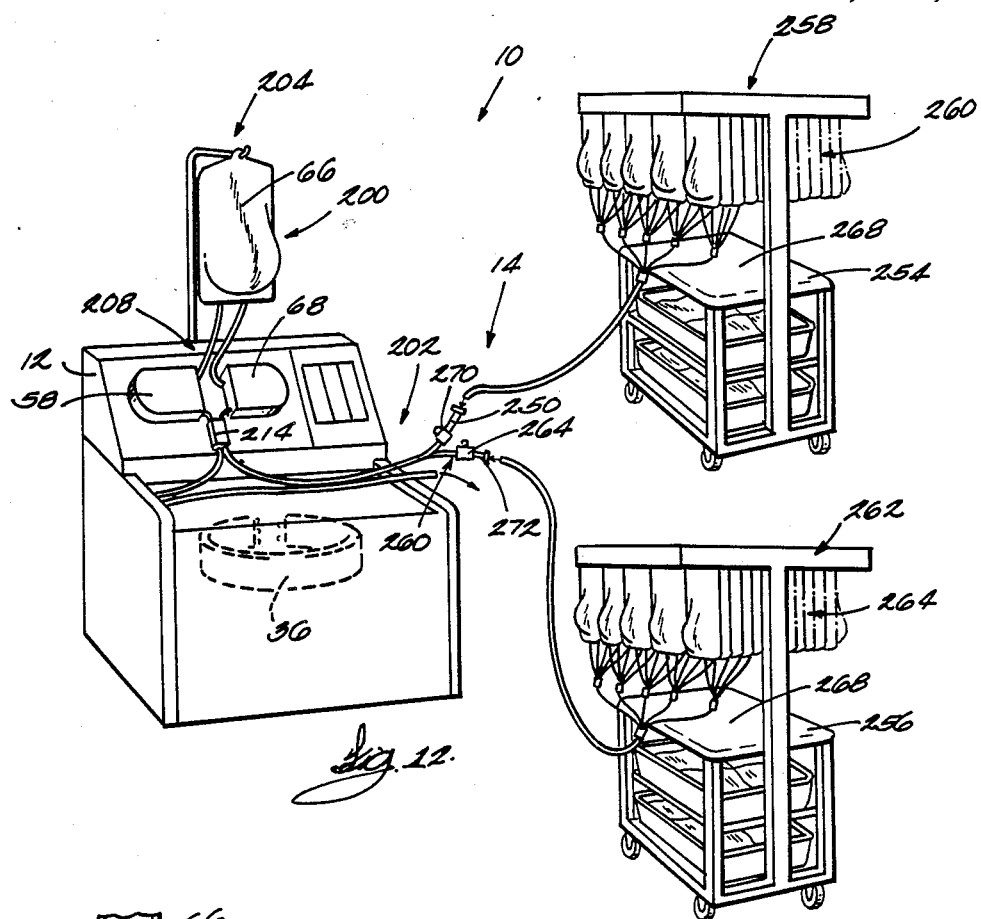
Fig. 12.
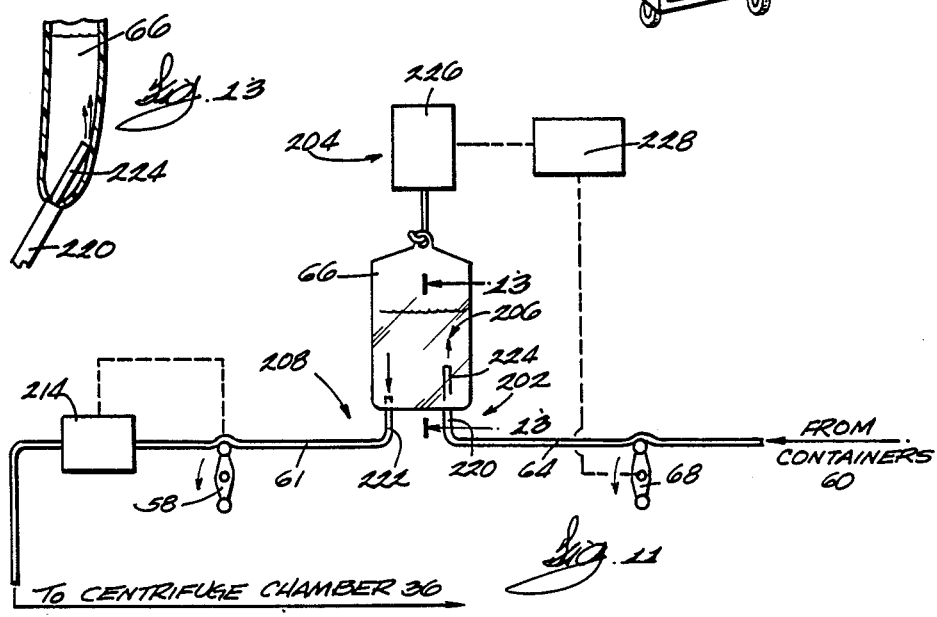
Fig. 13.
Fig. 11.

HIGH VOLUME CENTRIFUGAL FLUID PROCESSING SYSTEM AND METHOD FOR CULTURED CELL SUSPENSIONS AND THE LIKE

This application is a continuation of application Ser. No. 255,126, filed Oct. 7, 1988, now abandoned.

FIELD OF THE INVENTION

The invention generally relates to systems and methods for separating fluids by centrifugation. More particularly, the invention relates to the centrifugation of large volumes of fluids at relatively high flow rates. In this respect, the invention also relates to systems and methods particularly well suited for the processing of cultured cells and supernatant, such as in the fields of biotechnology and adoptive immunotherapy.

BACKGROUND OF THE INVENTION

Many fluid processing techniques entail the centrifugation of large volumes of fluids. To minimize processing times, these techniques often require the use of relatively high flow rates. Increasingly, such techniques are being used in the medical field.

For example, in the areas of biotechnology and adoptive immunotherapy, it is necessary to process relatively large volumes of cultured cellular products by centrifugation. Through centrifugation, cultured cells are separated from the supernatant for the purpose of replacing-/exchanging the culture medium; or for providing a cell-free supernatant for subsequent collection of antibodies or for subsequent use as an additive to culture mediums; or for the collection of concentrated cellular product.

In the area of adoptive immunotherapy, it has been possible to process between 10 to 50 liters of cultured LAK (Limphokine Activated Killer) cells at a rate of 175 ml/min using conventional centrifugation techniques and devices previously used in whole blood processing. However, in the processing of TIL (Tumor Infiltrating Lymphocytes), the volume of cultured cells that must be processed is increased by an order of magnitude to approximately 100 to 400 liters. Conventional blood processing techniques and devices cannot effectively deal with these large fluid volumes and the attendant need to increase the processing rates.

Furthermore, the necessarily high inlet flow rates can lead to confused, turbulent flow conditions within the centrifugation chamber. These flow conditions are not desireable, because they can interfere with sedimentation and separation within the centrifugal force field. Thus, despite the high inlet flow rates, the overall effectiveness and efficiency of the process suffers.

High inlet flow rates and resulting confused, turbulent flow conditions can also result in a non-uniform distribution of the fluid within the centrifugation chamber.

Often, then, it is necessary to reduce the inlet flow rate below the desired amount in the interest of obtaining the flow conditions within the processing chamber conducive to optimal separation.

SUMMARY OF THE INVENTION

The invention provides systems and methods for centrifugally processing large volumes of fluid at relatively high flow rates without sacrificing separation efficiencies or damaging the end product.

One aspect of the invention provides a high volume centrifugal processing system for cultured cellular suspensions. The system comprises reservoir means for pooling a desired volume of the cellular suspension as well as first supply means for conveying cellular suspension into the reservoir means from a plurality of individual containers in which the cellular suspension have been cultured. The system further includes means controlling the first supply means for maintaining the desired volume of cellular suspension in the reservoir means during the processing period.

The system also includes means defining a centrifugation chamber operative in response to centrifugal force for separating the cellular suspension into a cellular component and a supernatant. Second supply means is provided for conveying fluid from the reservoir means into the centrifugation chamber at a generally high flow rate exceeding 1 liter per minute.

The system additionally includes means for collecting the cellular component and the supernatant from the centrifugation chamber.

In one embodiment, the means defining the centrifugation chamber comprises a tube having an inlet end communicating with the second supply means and an outlet end communicating with the cellular component collection means and the supernatant collection means. Preferably, the centrifugation chamber also includes means forming a passage in the tube adjacent to its inlet end for dispensing a uniform stream of fluid into the region of the tube where the least centrifugal forces exist. As used herein, the term "generally uniform" identifies a flow condition in which turbulence is reduced or eliminated to the fullest extent possible. In addition, means is preferably provided for creating within the tube a region confining the cellular component separated in response to the centrifugal field while allowing the supernatant to flow out of the outlet end of the tube.

In accordance with this aspect of the invention, the system establishes, upon the entry of high velocity fluid into the centrifugal field, non-turbulent and uniform flow conditions conducive to effective separation. The system also directs the fluid in a way the maximizes the effective surface area of the centrifugation chamber for separation. Effective separation can thereby be achieved at high inlet flow rates.

In another embodiment, the first supply means of the centrifugal processing system comprises a pump, and the means for controlling the first supply means comprises means operatively connected with the pump for sensing the weight of the reservoir means and for controlling operation of the pump based upon the sensed weight. Preferably, the reservoir means also includes means for removing air from the fluid conveyed into the reservoir means.

In another embodiment, the second supply means associated with the system includes means for sensing the fluid pressure and for controlling the introduction of fluid into the centrifugation chamber based on the sensed pressure.

Another aspect of the invention provides a work station particularly well suited for the processing of large volumes of fluid. The work station includes means for supporting a first plurality of cellular suspension containers in fluid communication with the first supply means during fluid processing. The work station also includes a work surface for accommodating the manipulation of the cellular suspension containers during the processing period.

In one preferred embodiment of the invention, the first supply means includes first and second inlets. In this arrangement, two work stations are provided. The first work station includes means for supporting a first plurality of cellular suspension containers in fluid communication with the first inlet of the first supply means during fluid processing. The second work station likewise includes means for supporting a second plurality of cellular suspension containers in fluid communication with said second inlet of said first supply means during fluid processing. Both work stations include a work surface for accommodating the manipulation of said pluralities of cellular suspension containers during the processing period.

In this arrangement, the first supply means further includes means for conveying cellular suspension into the reservoir means through a selected one or both of the first and second inlets. The work stations thus serve, in association with the multiple inlets, to provide an uninterrupted flow of fluid on a large volume basis.

The invention also provides a method for centrifugally processing large volumes of cultured cellular suspensions. This method comprises the steps of supporting a first plurality of cellular suspension containers in fluid communication with a reservoir, and conveying the cellular suspension from the first plurality of containers into the reservoir. A desired volume of cellular suspension is maintained in the reservoir while conveying the cellular suspension into a centrifugation chamber. In response to centrifugal forces in the chamber, the cellular suspension is separated into a cellular component and a supernatant. While the cellular suspension from the first plurality of containers is being centrifugally processed, a second plurality of cellular suspension containers are readied for processing. After a desired quantity of the cellular suspension from the first plurality of containers has undergone processing, the flow of cellular suspension from the second plurality of containers is begun to continue the centrifugal processing without interruption.

Other features and advantages of the invention will become apparent upon considering the accompanying drawings, description, and claims.

BRIEF DESCRIPTION OF THE DRAWINGS

FIG. 1 is a perspective view of a fluid processing system embodying the features of the invention and particularly adapted for the harvesting of TIL cells in a high volume basis;

FIG. 2 is a schematic side view, fragmented and partially in section, of a portion of the centrifugal processing system shown in FIG. 1;

FIG. 3 is a top view of the centrifugal processing system taken generally along line 3—3 in FIG. 2;

FIG. 4 is an enlarged fragmented top view of the processing tube or envelope of the fluid processing set associated with the system shown in FIG. 1;

FIG. 5 is a side view of the processing tube or envelope taken generally along line 5—5 in FIG. 4;

FIG. 6 is an exploded perspective view of the processing tube shown in FIG. 2 showing the associated flow control means;

FIG. 7 is an enlarged schematic view, fragmented and broken away in section, of the processing tube or envelope shown in FIGS. 4 to 6 illustrating the flow of fluid through the tube or envelope when it is in use in a centrifugal field;

FIG. 8 is a greatly enlarged schematic view, fragmented and in section, of the collection of higher density materials in the tube or envelope shown in FIG. 7;

FIG. 9 is a centrifugal fluid processing system embodying the features of the invention and intended to be use in the harvesting of cell cultures on a large volume basis;

FIG. 10 is an alternate embodiment of a centrifugal fluid processing system embodying the features of the invention;

FIG. 11 is an enlarged schematic view of a portion of the fluid processing system shown in FIG. 1, showing the inlet and outlet fluid control mechanisms;

FIG. 12 is a schematic view of a system which embodies the features of the invention being used in association with two work stations; and FIG. 13 is an enlarged side section view of the reservoir bag associated with the system taken generally line 13—13 in FIG. 11.

DESCRIPTION OF THE PREFERRED EMBODIMENTS

A centrifugal fluid processing system 10 embodying the features of the invention is shown in FIG. 1. The system 10 includes a centrifuge 12, an associated fluid processing set 14, and an associated work station 15. In the illustrated and preferred embodiment, the set 14 is disposable, intended to be used once and then discarded.

The system 10 can be used to process many different types of fluid. As will become apparent, the system 10 is capable of efficiently processing large volumes of fluid at relatively high flow rates. At the same time, the system 10 is well adapted to handle fluids requiring special handling, such as those containing living cells or delicate organisms, like blood or cultured cell suspensions, both on a clinical basis and an industrial basis. For this reason, the system 10 is particularly well suited for use in the medical field.

As illustrated in FIG. 1, the system 10 is particularly arranged for use to harvest cultured TIL cells. The set 14 is particularly configured for this intended use and is also shown in FIG. 9.

As configured for processing large volumes of cultured cellular suspensions, the system 10 comprises reservoir means 200 for pooling a desired volume of the cellular suspension. First supply means 202 is also provided for conveying cellular suspension into the reservoir means 200 from a plurality of individual containers 60 in which the cellular suspension have been cultured.

The system 10 further includes means 204 controlling the first supply means 202 for maintaining the desired volume of cellular suspension in the reservoir means 200 during the processing period.

The system 10 also includes means defining a centrifugation chamber 36 operative in response to centrifugal force for separating the cellular suspension into a cellular component and a supernatant. Second supply means 208 is provided for conveying fluid from the reservoir means 200 into the centrifugation chamber at a generally high flow rate exceeding 1 liter per minute.

The system 10 additionally includes means 210 for collecting the cellular component and means 212 for collecting the supernatant from the centrifugation chamber 36.

In the illustrated embodiment, the first supply means 202 of the centrifugal processing system 10 includes a supply pump 68. As will be described in greater detail below, the means 204 for controlling the first supply means 202 comprises means operatively connected with the pump 68 for sensing the weight of the reservoir means 200 and for controlling operation of the supply pump 68 based upon the sensed weight.

As will also be described in greater detail below, the reservoir means 200 takes the form of a bag 66 which also includes means 206 for removing air from the fluid conveyed into the reservoir means 200.

As will be further described in greater detail below, the second supply means 208 associated with the system 10 includes means 214 for sensing the fluid pressure and for controlling the introduction of fluid into the centrifugation chamber 36 based on the sensed pressure.

What follows is a general overview of a typical TIL harvesting procedure using the system 10 as just described. In a TIL harvesting procedure using the system 10, cultured TIL cell solution filling approximately 70 to 260 three liter bags 60, each filled with about 1½ liters of solution, is centrifugally processed to remove the supernatant and obtain concentrated TIL cells (which presently consists of approximately $2 \times 10^{11}$ cells occupying a volume which ranges between 200 to 400 ml).

In this arrangement, the first supply means 202 includes 5-lead and 10-lead manifold sets 62 that interconnect the many supply bags 60 to a single inlet line 64. The cultured cell fluid is then conveyed into the reservoir bag 66, using the supply pump 68.

The fluid is then conducted, via the pressure monitor means 214 into the centrifugal processing chamber 36 by means of a processing pump 58.

In this arrangement, and as will be described in greater detail below, the processing chamber 36 is in the form of a tube 34 that is approximately 32 inches long and 3 inches wide.

During centrifugation, the TIL cells are separated from the culture medium (which constitutes the supernatant). The supernatant is collected in large volume containers 212. Afterwards, the concentrated TIL cells are transferred to a collection container 210 for administration to the patient.

The centrifuge 12 can be variously constructed. However, in the illustrated embodiment, the centrifuge 12 is shown to incorporate the principles of operation disclosed in Adams U.S. Pat. No. Re 29,738.

In this arrangement (as best shown in FIG. 2), the centrifuge 12 includes a processing assembly 16 and a rotor assembly 18 each of which independently rotates about the same axis 20. The processing assembly 16 is connected to a first drive shaft 22. The rotor assembly 18 is connected to a second drive shaft 28. The second drive shaft is driven via a suitable pulley assembly 24 by a drive motor 26. The first drive shaft 22 is driven by a suitable pulley assembly 30 associated with the second drive shaft 28.

The pulley assemblies 24 and 30 are conventionally arranged to cause the processing assembly 16 to rotate in the same direction as and at twice the rotational speed of the rotor assembly 18. Examples of this type of construction are more fully disclosed in Lolachi U.S. Pat. No. 4,113,173.

As can be best seen in FIGS. 2 and 3, the processing assembly 16 includes an inner processing area 32. The processing area 32 takes the form of an arcuate slot or channel. The slot 32 can be configured in various ways, depending upon the intended use of the system. In the illustrated embodiment (best shown in FIG. 3), the slot 32 is generally equally radially spaced about the rotational axis 20 shared by processing assembly 16 and rotor assembly 18.

With further reference now to FIGS. 4 to 6, the fluid processing set 14 includes an envelope or tube 34 defining a hollow interior chamber 36 having an inlet end 38 and an outlet end 40. The tube 34 is intended to be inserted into the processing slot 32 (see FIGS. 3 and 4). As will be soon described in greater detail below, the intended centrifugal separation of the processed fluid occurs within the interior chamber 36 of the tube 34 due to centrifugal forces created during rotation of the processing assembly 16.

The tube 34 can be made from either a flexible or rigid material. When flexible, the tube 34 can be readily fitted into the slot 32 to there conform to the particular configuration of the slot 32. When rigid, the tube can be preformed to conform to the particular configuration of the slot 32. In the illustrated embodiment, which contemplates use of the system 10 in the medical field, the tube 34 is made from a flexible medical grade plastic material, such a polyvinyl chloride.

As best shown in FIG. 3, the fluid processing set 14 further includes inlet tubing 42 for conveying fluid into the inlet end 38 of the tube chamber 36 for centrifugal separation. Likewise, the set 14 includes outlet tubing 44 for conveying fluid constituents from the outlet end 40 of the tube chamber 36 after processing.

In the illustrated embodiment, there are two inlet tubes 42 and three outlet tubes 44 (see FIG. 4). Of course, the number of tubes can vary according to the intended use and function of the system 10.

In the illustrated embodiment, the inlet and outlet tubing 42 and 44 are made from flexible medical grade plastic material and are joined to form a multiple lumen umbilicus 46. As best shown in FIG. 2, the umbilicus 46 is suspended from a point above and axially aligned with the rotational axis 20 of the centrifuge 12 by means of a clamp 48 attached to a support arm 50. From this point, the umbilicus 46 extends generally downwardly and radially outwardly, passing against a guide arm 52 carried by the rotor assembly 18. From there, the umbilicus 46 extends generally downwardly and radially inwardly and then upwardly through the hollow center of the drive shaft 22 into the processing assembly 16.

This looping arrangement of the umbilicus 46, coupled with the differing rotational rates of the processing assembly 16 and the rotor assembly 18 as just described, prevents the umbilicus 46 from becoming twisted during operation of the centrifuge 12. The use of rotating seals between the fixed and rotating parts of the system 10 is thereby avoided. However, it should be appreciated that the invention is applicable for use in other types of centrifugal systems, including those employing rotating seals.

Once the tube 34 is located in the processing area 32 and filled with fluid, the rotation of the processing assembly 16 will create a centrifugal force field F (see FIG. 3) effecting the contents of the tube chamber 36. This force field F will create a "High G Region" 54 and a "Low G Region" 56 within the chamber 36. As shown in FIG. 3, the "High G Region 54" is located adjacent to the outer wall of the chamber 36, where the force field is farthest away from the rotational axis and the contents of the chamber 36 are subjected to the highest rotational (or "G") forces. The "Low G Region 56" is located adjacent to the inner wall of the chamber 36, where the force field is nearer to the rotational axis and the contents of the chamber are subjected to lesser rotational (or "G") forces. As best shown in FIGS. 7 and 8, higher density materials present in the processed fluid (designated 101 in FIGS. 7 and 8) will migrate under the influence of the force field F toward the High G Region 54, leaving the less dense materials and supernatant (designated 115 in FIGS. 7 and 8) behind in the Low G Region 56.

To obtained the desired flow rate conditions, the fluid to be processed is introduced into the tube chamber 36 using the in line processing pump 58. In the illustrated embodiment (see FIGS. 2 and 9), the pumping mechanism takes the form of a peristaltic pump 58 situated upstream of the tube chamber 36.

In this and other applications, where relatively large volumes of fluid are to be processed, it is desirable to maximize the inlet flow rate of the fluid, as this will shorten the overall processing time. In the case of a TIL procedure, a nominal processing rate of at least 1.5 liters per minute is attained. With the system illustrated herein, it is believed that the processing rates can be further increased upwards to about 4 liters per minute. This rate is significantly higher than the nominal processing rates conventionally used for blood processing (about 50 ml/min) or conventionally used for TIL cell harvesting (about 175 ml/min).

Use of these relatively high inlet flow rates can pose processing problems. In particular, such high rates can lead to confused, turbulent flow conditions within the tube chamber 36. These turbulent or otherwise confused, non-uniform flow conditions can interfere with sedimentation and separation within the centrifugal force field F, lowering the overall effectiveness and efficiency of the process.

High inlet flow rates and attendant confused, turbulent flow conditions can also result in a non-uniform distribution of the fluid within the tube chamber 36. To maximize the effective surface area along which separation occurs, the incoming fluid should preferably enter in the Low G Region 56 as soon as possible after entering the tube 34. The fluid components are thereby exposed to the full extent of the centrifugal force field F for the longest period of time. However, high inlet flow rates can spray or disperse the incoming fluid indiscriminately into both the High and Low G Regions 54 and 56 of the tube 34. This, too, lowers the overall effectiveness and efficiency of the process.

To optimize the effectiveness of separation at high inlet flow rates, the invention provides a fluid processing system 10 that includes means 76 located adjacent the inlet end of the tube chamber 36 for directing incoming fluid away from the High G Region 54 and toward the Low G Region 56 of the chamber 36 in a uniform flow generally free of turbulence. Preferably, the uniform flow constitutes a relatively thin stream filling the entire effective surface area of the Low G Region 56 adjacent to the inlet end of the chamber 36.

In accordance with the invention, the means 76 therefore establishes, upon the entry of high velocity fluid into the centrifugal field F, the desired flow conditions for effective separation. The means 76 also directs and dispenses the fluid in a manner that maximizes the effective surface area of the tube chamber 36 for separation. Due to the invention, effective separation can be achieved, even at high inlet flow rates.

The means 76 can be variously constructed. One embodiment is shown in FIGS. 4 to 6. In this arrangement, the means 76 is part of a port block assembly 78 situated within the inlet end 38 of the tube chamber 36. The assembly 78 includes top, bottom, and side walls 80; 81; and 82 defining an open interior 84. The assembly 78 also includes a first end wall 86 closing the adjacent end of the interior 84. One or more inlet ports 88 are formed on this end wall 86. The inlet tubing 42 is attached to these ports 88 to introduce fluid into the open interior 84 of the assembly 78.

In this arrangement, the means 76 comprises a partial second end wall 90 located on the end of the port block assembly 78 opposite to the end wall 86 on which the inlet ports 88 are situated. This partial end wall 90 extends from the top wall 80 toward the bottom wall 81, terminating a short distance therefrom to there define a passage 92 communicating with the open interior 84 of the assembly 78. As will be described in greater detail below, fluid introduced into the open interior 84 of the port block assembly 78 (via the inlet ports 88) is directed into the centrifugal force field through the passage 92.

As best shown in FIG. 5, the port block assembly 78 is situated within the inlet end of the tube chamber 36 with the passage 92 extending longitudinally across the entire interior surface of the tube chamber 36 which, in use, becomes the Low G Region 56.

To assure that the interior surface of the tube 34 becomes the Low G Region 56 when situated within the processing area 32, a guide key 94 is provided on the port block assembly 78 which mates with a groove 96 in the processing area 32 (see FIG. 3) when the tube 34 is properly oriented.

The system 10 further includes means 98 defining a region 100 for collecting high density materials within the tube chamber 36. In the embodiment shown in FIGS. 3 to 6, the means 98 includes a dam assembly 102 situated within the tube chamber 36 downstream of the port block assembly 78. The dam assembly 102 may be variously constructed. In the illustrated embodiment, the dam assembly 102 is part of another port block assembly as previously described. The assembly 102 includes top and bottom walls 103/104, side walls 105, and an end wall 106.

In this arrangement, the dam assembly 102 comprises a partial end wall 108, which like the means 76 associated with the port block assembly 78, forms another passage 110 through which fluid must pass to exit the tube chamber 36.

The length of the end wall 108 associated with the dam assembly 102 can vary. It can be the same as or different than the end wall 90 of the port block assembly 78, depending upon the nature and type of collection area or areas sought to be established within the tube chamber 36. The sedimentation of higher density materials in the region 100 is also effected by the fluid flow rate, the RPM of the centrifuge, and the interior thickness of the tube chamber 36. These variables can be adjusted to alter the collection characteristics of the tube 34.

It should also be appreciated that multiple dam assemblies of varying lengths and spacing can be used to create multiple separation and sedimentation zones within the tube chamber 36.

As shown in FIGS. 7 and 8, and as will be described in greater detail below, the higher density materials (designated 101 in FIGS. 7 and 8) migrating toward the High G Region 54 of the chamber 36 will collect within the area 100 bounded by the partial end wall 90 of the port block assembly 78 and the partial end wall 108 of the dam assembly 102.

In the embodiment shown in FIGS. 4 to 6, the dam assembly 102 is located in the outlet end 40 of the tube chamber 36, and outlet ports 112 are accordingly formed on the end wall 106, as in the port block assembly 78. However, it should be appreciated that the dam assembly 102 can be located within the tube chamber 36 at a location upstream of the outlet end 40 of the chamber 36 (as shown in FIG. 7), in which case the end wall 106 would be free of ports. In this arrangement, a separate port block assembly (not shown), without a partial end wall, would be used at the outlet end 40 of the tube chamber 36.

The port block assembly 78 and the dam assembly 102 can be made of various materials. In the illustrated embodiment, both are injection molded plastic parts that are located and sealed within the confines of the tube chamber 36 by heat sealing, solvent sealing, or similar techniques.

The dimensions of the passages 92 and 110 can vary according to the type of fluid being processed and the flow conditions desired. In the particular embodiment shown in FIG. 9, the passages 92 and 110 are each about 3 inches wide (the same width as the associated tube) and about 0.025 inch in height.

Another embodiment of the means 76 for directing incoming fluid toward the Low G Region 56 is shown in FIG. 10. In this arrangement, the means 76 takes the form of a ridge 114 formed within the outside (High G) side of the processing area 32 of the assembly 16. When the tube 34 is positioned within the processing area 32 (as shown in FIG. 8), the ridge 114 presses against the exterior of the outside wall of the tube 34, thereby forming a passage 92 like that formed by the partial end wall 90 of the port block assembly 78. Preferably, a recess 116 is formed in the inside (Low G) side of the processing area 32 radially across from the ridge 114 to facilitate insertion and removal of the tube 34 and to better define the passage 92.

As also shown in FIG. 10, the means 98 for defining the collection area 100 for higher density materials can also take the form of a ridge 118 and associated recess 120 formed along the walls of the processing area 32 of the centrifuge 12.

Due to the operation of the above described port block assembly 78 and dam assembly 102, as the fluid to be processed is introduced into the centrifugal force field F, it is directed away from the region of the chamber 36 where the largest centrifugal (or "G") forces exist. Furthermore, the fluid is directed and dispensed into the force field as a generally uniform stream (designated by arrows and number 111 in FIGS. 7 and 8) essentially free of turbulence.

Referring specifically now to FIGS. 7 and 8, incoming fluid entering the port block assembly 78 (via the ports 88) is immediately confined within the open interior 84. Turbulent flow conditions occasioned by the entry of fluid into the chamber 36 (indicated by swirling arrows 113 in FIGS. 7 and 8) are thereby effectively confined to this interior area 84 and isolated from the remainder of the tube chamber 36.

The fluid confined within the interior area 84 is directed by the partial end wall 90 away from the High G Region 54 and out into the tube chamber 36 via the passage 92. By virtue of the shape of the passage 92, the fluid is directed and dispensed in a generally uniform stream 111 extending across the Low G Region 56 of the tube chamber 36.

Optimal conditions for sedimentation and separation are thereby quickly established. As a result, the higher density materials 101 migrate due to the force field F toward the High G Region 54. The remaining supernatant (designated by arrows and number 115 in FIGS. 7 and 8) continues to flow uniformly along the Low G Region 56 toward the outlet end 40 of the tube chamber 36.

The process also creates within the chamber 36 a region 100 where the higher density materials 101 collect, while allowing the supernatant 115 to flow freely out of the chamber 36. As can be best seen in FIG. 7, the higher density materials 101 migrating toward the High G Region 54 of the chamber 36 collect within the area 100 bounded by the partial end wall 90 of the port block assembly 78 and the partial end wall 108 of the dam assembly 102. At the same time, the supernatant, which is free of the higher density materials 101, passes through the passage 110 of the dam assembly 102 and exits the outlet end 40 of the tube chamber 36.

Referring now to FIG. 11, the reservoir bag 66 includes an inlet port 220 which communicates with the inlet line 64 for conveying fluid into the bag 66. The bag 66 also includes an outlet port 222 which communicates with the outlet line 61 for conveying fluid from the bag 66 and into the tube 34.

The outlet tube 61 is preferably includes an interior bore of at least 0.25 inch to accommodate the desired large volume fluid flow. The tube 61 runs through the peristaltic processing pump 58, and connects to the inlet tubes 42 which enter the umbilicus 46. The inlet tubes 42 are typically smaller in internal diameter than the outlet tube 61. The outlet tube 61 also runs through a non-invasive pressure monitor 214, which monitors fluid pressure through the wall of the tube 61.

As can be seen in FIG. 11, the inlet port 220 of the reservoir bag 66 includes a portion 224 that extends into the interior of the bag 66, whereas the outlet port 222 does not. This port arrangement serves to effectively isolate the inlet and outlet ports 220 and 222 from each other. As shown in FIG. 13, incoming solution is directed upward through the extended portion 224 of the inlet port 220 and against the interior wall of the bag 66 to "fan out" the incoming solution flow (shown by arrows in FIG. 13). This flow prevents foaming. At the same time, air bubbles are released into the interior of the bag 66. The reservoir bag 66 thereby also serves as a high flow rate bubble trap.

As also shown in FIG. 11, the means 204 for controlling the first supply means 202 includes a weight transducer 226 associated with the reservoir bag 66. The transducer 226 senses the weight of the bag 66. The weight is monitored by a control circuit 228 and compared to a predetermined value. When the transducer output exceeds this predetermined value, a control signal is produced which stops the supply pump 68. The introduction of additional fluid into the bag 66 terminates while operation of the processing pump 58 continues to remove fluid from the bag 66. The weight of the bag 66 will thus be reduced. When the transducer output falls below the predetermined value, a new control signal resumes operation of the supply pump 68. In this fashion, the volume of fluid contained in the bag 66 is maintained within a desired range.

Should the transducer output fall below a second predetermined value lower than the predetermined value discussed in the preceding paragraph, a control signal is generated which terminates operation of the supply pump 68. Thus, the transducer 226 will sense when fluid in the supply bags 60 is depleted, and will terminate operation of the pump 68 to prevent the introduction of air into the fluid flow system.

As further shown in FIG. 11, the pressure monitor 214 senses system pressure to alert the operator of a blocked line or an air block in the centrifuge portion 12 of the system 10. The system pressure is typically 22 psi at a flow rate of 1500 ml per minute and a centrifuge speed of 1600 rpm. If this pressure increases to 35 psi, the processing pump 58 is shut off and the centrifuge speed is decreased. This lowers the internal system pressure in the centrifuge area of the system 10, and allows for the air blockage to flow through the set 14. When the system pressure has dropped to approximately 22 psi, the centrifuge speed is increased and the processing pump 58 is restarted.

When performing a TIL procedure, many bags 60 of cultured cells must be taken from an incubator (usually several incubators) where they have been cultured. Since handling, transport to the harvester and bag preparation is time consuming, it is important to simplify this process. The invention provides the work station 15 to facilitate this task. The work station 15 is particularly well suited for the processing of large volumes of fluid.

As shown in FIG. 1, the work station 15 includes means 230 for supporting a first plurality of cellular suspension containers (generally designated 60) in fluid communication with the first supply means 202 during fluid processing. The work station 15 also includes means 232 for storing cellular suspension containers (generally designated 234) until it is time to process them. The work station 15 also includes a work surface 236 for accommodating the manipulation of said pluralities of cellular suspension containers 60 and 234.

In the illustrated embodiment, the work station 15 is a cart-like device which has hangers 238 on top to hold approximately fifty (50) bags 60, each containing approximately 1500 ml of cultured cells. The bags 60 are hung in a vertical orientation to allow for complete draining of the contents during processing. The large number of bags comprising the first plurality 60 that can be hung on a single work station 15 maximizes the available working space and provides for a longer harvesting session.

The top surface 236 of the work station 15 serves as a flat tabletop for the organizing and manipulation which is required when preparing the bags for hanging and manifold connection.

The middle shelf 240 of the work station 15 holds a bin 242 for storing cultured cell bags 234 after removed from the incubator and prior to processing. Approximately 50 3 L bags can be taken from the incubator and placed into the bin 242, which conveniently holds these bags 234 prior to processing, keeping them from contacting the dirty environment while being transported to an area suitable for manifold connection.

The lower shelf 244 of the work station 15 can also contain bin 246 for large plastic containers 212 which collect the supernatant which is extracted from the cultured cells being processed. Because the cells are very dilute and occupy very little volume, approximately the same volume of supernatant is produced as cultured cells harvested. The collected supernatant can be further processed or used as an additive for other cell culture mediums. The collected supernatant call also be discarded. In most locations, supernatant is not allowed to be disposed of by pouring down a sanitary drain. Since special discard policies must be maintained, the collection of the supernatant in large containers on the mobile work station 15 makes it easy and convenient to collect and transport after the hanging bags have been processed.

The work station 15 is sturdily constructed of stainless steel for easy cleaning and maintenance. The bins 242 and 246 are removable and fabricated of an easily cleaned plastic.

A horizontal handle 248 is provided for easy control of the work station 15. Large front and rear wheels give the work station 15 mobility to easily manipulate within the usually tight laboratory conditions.

In the embodiment of the invention shown in FIG. 12, the first supply means 202 includes first and second inlets 250 and 252. In this embodiment, two work stations 254 and 256 are provided. The first work station 254 includes means 258 for supporting a first plurality of cellular suspension containers 260 in fluid communication with the first inlet 250 of the first supply means 202 during fluid processing. The second work station 256 includes means 262 for supporting a second plurality of cellular suspension containers 264 in fluid communication with said second inlet 252 of said first supply means 202 during fluid processing.

In this arrangement, the first supply means 202 further including means 260 for conveying cellular suspension into the reservoir means 200 through a selected one or both of the first and second inlets 250 and 252. In the illustrated embodiment, the means 260 takes the form of manually actuated clamps 270 and 272 associated with the first and second inlets 250 and 252, respectively.

The use of two work stations 254 and 256 thus serves, in association with the multiple inlets 250 and 252, to provide an uninterrupted flow of fluid on a large volume basis.

Both work stations 254 and 256 also include a work surface 268 for accommodating the manipulation of said pluralities of cellular suspension containers.

Another aspect of the invention provides a method for centrifugally processing large volumes of cultured cellular suspensions. This method comprises the steps of supporting a first plurality of cellular suspension containers 260 in fluid communication with a reservoir 66, using the first work station 254. The cellular suspension from the first plurality of containers 260 is conveyed into the reservoir 66. As before described, a desired volume of cellular suspension is maintained in the reservoir 66 while conveying the cellular suspension into a centrifugation chamber 36. In response to centrifugal forces in the chamber 36, the cellular suspension is separated into a cellular component and a supernatant.

While the cellular suspension from the first plurality of containers 260 is being centrifugally processed, a second plurality of cellular suspension containers 262 are readied for processing adjacent to the reservoir, using the second work station 256. After substantially all or a desired quantity of the cellular suspension from the first plurality of containers 260 has undergone processing, the flow of cellular suspension from the second plurality of containers 264 can commence to continue the centrifugal processing without interruption.

EXAMPLE 1

A system 10 embodying the features of the invention was used in association with a set as generally shown in FIG. 9 and an Adams-type centrifuge to harvest human red blood cells from a saline suspension. Three runs were conducted.

In the first run, the suspension had an original red blood cell concentration of $1.27 \times 10^7$ per ml. This suspension was centrifugally processed through the tube at a flow rate of 1800 ml/min at 1600 RPM. During processing, red blood cells were collected at a processing efficiency of 94.9%.

In the second run, the original suspension concentration was $1.43 \times 10^7$ red blood cells per ml. During centrifugal processing at a flow rate of 1000 ml/min at 1600 RPM, concentrated red blood cells were collected at a processing efficiency of 95.7%.

In the third run, the original suspension concentration was $1.33 \times 10^7$ red blood cells per ml. During centrifugal processing at a flow rate of 1800 ml/min at 1600 RPM, concentrated red blood cells were collected at a processing efficiency of 91.5%.

EXAMPLE 2

A system 10 embodying the features of the invention was used in association with a set as generally shown in FIG. 9 and an Adams-type centrifuge to harvest TIL cells from suspension.

During the procedure, 24,559 ml of cultured TIL cell suspension was processed through the tube a flow rates varying between 500 to 1500 ml/min at 1600 RPM. 445 ml of concentrated TIL cells were obtained.

Approximately $564.9 \times 10^8$ TIL cells were contained in the suspension prior to processing. During processing, approximately $462.8 \times 10^8$ TIL cells were collected, for a processing efficiency of 82%.

TIL cell viability of 73% was measured prior to processing. TIL cell viability of 73% was measured after processing.

Lytic activity of the TIL cells prior to processing was 5.4%. After processing, the lytic activity was 4.3%, which is not a statistically significant difference.

The foregoing examples clearly illustrate the ability of a processing system made and operated in accordance with the invention to efficiently process large volumes of cellular suspensions at relatively high fluid flow rates. Example 2 further demonstrates the processing occurs without causing any biological damage to the cellular components.

Various features of the invention are set forth in the following claims.

I claim:

1. A centrifugal processing system for cultured cellular suspensions comprising
    reservoir means for pooling a desired volume of the cellular suspension;
    first supply means for conveying cellular suspension into said reservoir means from a plurality of individual containers in which the cellular suspension have been cultured;
    means controlling said first supply means for maintaining said desired volume of cellular suspension in said reservoir means during the processing period;
    means defining a centrifugation chamber operative in response to centrifugal force for separating the cellular suspension into a cellular component and a supernatant;
    second supply means for conveying fluid from said reservoir means into said centrifugation chamber;
    means for collecting the cellular component from said centrifugation chamber; and
    means for collecting the supernatant from said centrifugation chamber.

2. A centrifugal processing system according to claim 1 wherein said means defining said centrifugation chamber comprises a tube having an inlet end communicating with said second supply means and an outlet end communicating with said cellular component collection means and said supernatant collection means.

3. A centrifugal processing system according to claim 2 wherein said means defining said centrifugation chamber includes means forming a passage in said tube adjacent to its inlet end for dispensing a uniform stream of fluid essentially free of turbulence into the region of the tube where the least centrifugal forces exist.

4. A centrifugal processing system according to claim 2 wherein said means defining said centrifugation chamber includes means for creating within said tube a region confining the cellular component separated in response to the centrifugal field while allowing the supernatant to flow out of the outlet end of said tube.

5. A centrifugal processing system according to claim 1 wherein said first supply means comprises a pump; and
    wherein said means for controlling said first supply means comprises means operatively connected with said pump for sensing the weight of said reservoir means and for controlling said pump based upon the sensed weight.

6. A centrifugal processing system according to claim 1 wherein said reservoir means includes means for removing air from the fluid conveyed into said reservoir means.

7. A centrifugal processing system according to claim 1 wherein said second supply means includes means for sensing the fluid pressure and for controlling the introduction of fluid into said centrifugation chamber based on the sensed pressure.

8. A centrifugal processing system according to claim 1 and further including
    a work station including
        means for supporting a first plurality of cellular suspension containers in fluid communication with said first supply means during fluid processing, and
        means defining a work surface for accommodating the manipulation of said pluralities of cellular suspension containers.

9. A centrifugal processing system according to claim 8 wherein said work station further includes means for holding said means for collecting the supernatant.

10. A centrifugal processing system according to claim 8 wherein said work station further includes means for transporting said work station to and from the site of processing.

11. A centrifugal processing system for cultured cellular suspensions comprising reservoir means for pooling a desired volume of the cellular suspension;

first supply means for conveying cellular suspension into said reservoir means from a plurality of individual containers in which the cellular suspension have been cultured, said first supply means including a first inlet and a second inlet;

means controlling said first supply means for maintaining said desired volume of cellular suspension in said reservoir means during the processing period;

means defining a centrifugation chamber operative in response to centrifugal force for separating the cellular suspension into a cellular component and a supernatant;

second supply means for conveying fluid from said reservoir means into said centrifugation chamber;

a first work station including
  means for supporting a first plurality of cellular suspension containers in fluid communication with said first inlet of said first supply means during fluid processing, and
  means defining a work surface for accommodating the manipulation of said plurality of cellular suspension containers on said first work station, a second work station including
  means for supporting a second plurality of cellular suspension containers in fluid communication with said second inlet of said first supply means during fluid processing, and
  means defining a work surface for accommodating the manipulation of said plurality of cellular suspension containers on said second work station, and said first supply means further including means for conveying cellular suspension into said reservoir means through a selected one or both of said first and second inlets.

12. A centrifugal processing system according to claim 11 and further including
means on each of said first and second work stations for collecting the supernatant from said centrifugation chamber.

13. A centrifugal processing system according to claim 11
wherein each of said first and second work stations further includes means for transporting said respective work station to and from the site of processing.

14. A method for centrifugally processing large volumes of cultured cellular suspensions comprising the steps of:
  supporting a first plurality of cellular suspension containers in fluid communication with a reservoir,
  conveying the cellular suspension from the first plurality of containers into the reservoir;
  maintaining a desired volume of cellular suspension in the reservoir means while conveying the cellular suspension into a centrifugation chamber operative in response to centrifugal force for separating the cellular suspension into a cellular component and a supernatant;
  while the cellular suspension from the first plurality of containers is being centrifugally processed, supporting a second plurality of cellular suspension containers adjacent to the reservoir, and
  after a desired quantity of the cellular suspension from the first plurality of containers has undergone centrifugal processing, conveying cellular suspension from the second plurality of containers into the reservoir to continue centrifugal processing without interruption of fluid flow to the centrifugal chamber.

15. A centrifugation method according to claim 14 wherein, in said step of conveying cellular suspension to the centrifugation chamber, fluid is conveyed at a flow rate of at least 1 liter per minute.

16. A centrifugation method according to claim 14 and further including the steps of:
  collecting the cellular component from the centrifugation chamber, and
  collecting the supernatant from the centrifugation chamber.

* * * * *